United States Patent
Dockner et al.

(10) Patent No.: US 6,207,022 B1
(45) Date of Patent: *Mar. 27, 2001

(54) PURIFICATION OF CRUDE (METH) ACRYLIC ACID

(75) Inventors: Toni Dockner, Meckenheim; Gerhard Nestler, Ludwigshafen; Holger Herbst, Frankenthal; Helmut Lermer, Ludwigshafen; Hans Martan, Frankenthal; Herbert Vogel, Ludwigshafen; Herbert Exner, Waldsee, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/319,667

(22) Filed: Oct. 7, 1994

(30) Foreign Application Priority Data

Oct. 15, 1993 (DE) .................................................. 43 35 172

(51) Int. Cl.$^7$ ................................. B01D 3/34; C07C 51/44
(52) U.S. Cl. ................................ 203/38; 203/59; 203/60; 203/61; 203/DIG. 21; 562/600
(58) Field of Search ................................ 203/100, 6, 7, 203/38, 34, 59, 57, 91, 60, DIG. 21, 61; 562/600

(56) References Cited

U.S. PATENT DOCUMENTS

| 3,658,895 | 4/1972 | Riemann et al. | 260/530 |
|---|---|---|---|
| 3,932,500 | 1/1976 | Duembgen et al. . | |
| 4,625,500 | 12/1986 | Shibano et al. . | |
| 4,828,652 | 5/1989 | Schropp . | |
| 5,087,744 | 2/1992 | Krabetz et al. . | |
| 5,144,091 | 9/1992 | Martan et al. | 568/479 |
| 5,231,226 | 7/1993 | Hammon et al. | 562/534 |

FOREIGN PATENT DOCUMENTS

| 2 136 396 | | 10/1974 | (DE) . |
|---|---|---|---|
| 22 07 184 | | 7/1980 | (DE) . |
| 248250 | * | 8/1987 | (DE) . |
| 102 642 | | 1/1986 | (EP) . |
| 169 254 | | 11/1987 | (EP) . |
| 270 999 | | 6/1988 | (EP) . |
| 297 445 | | 1/1989 | (EP) . |
| 000014 | * | 1/1975 | (JP) . |
| 48438 | * | 3/1984 | (JP) . |
| 644505 | * | 1/1989 | (JP) . |

* cited by examiner

*Primary Examiner*—Virginia Manoharan
(74) *Attorney, Agent, or Firm*—Keil & Weinkauf

(57) ABSTRACT

Crude (meth)acrylic acid is purified by a process in which a primary amine compound and an organic sulfonic acid are added to the crude (meth)acrylic acid and the latter is then worked up by distillation.

6 Claims, No Drawings

PURIFICATION OF CRUDE (METH) ACRYLIC ACID

DESCRIPTION

The present invention relates to a process for separating aldehydes from crude (meth)acrylic acid which has been produced by the catalytic gas-phase oxidation method, in which a primary amine and/or a salt thereof is or are added to the crude (meth)acrylic acid, and the (meth)acrylic acid is separated from the mixture by distillation.

(Meth)acrylic acid is used as abbreviated notation and means acrylic acid or methacrylic acid. A primary amine is understood to mean a compound containing at least one —$NH_2$ group.

(Meth)acrylic acid, either as such or in the form of its esters, is particularly important for the preparation of polymers for a wide range of applications, for example for use as adhesives.

(Meth)acrylic acid is obtainable, inter alia, by catalytic gas-phase oxidation of alkanes, alkanols, alkenes or alkenals which contain 3 or 4 carbon atoms. (Meth)acrylic acid is particularly advantageously obtainable, for example, by catalytic gas-phase oxidation of propene, acrolein, tert-butanol, isobutene, isobutane, isobutyraldehyde or methacrolein. However, other possible starting compounds are those from which the actual $C_4$ starting compound first forms as an intermediate during the gas-phase oxidation. An example is the methyl ether of tert-butanol. These starting gases, as a rule diluted with inert gases, such as nitrogen, $CO_2$, saturated hydrocarbons and/or steam, are mixed with oxygen and passed at elevated temperatures and, if required, superatmospheric pressure over transition metal mixed oxide catalysts and converted oxidatively into (meth)acrylic acid, and the latter is separated from the product gas stream by absorption in a suitable absorbent (for example water or a mixture of from 70 to 75% by weight of diphenyl ether and from 25 to 30% by weight of biphenyl) (cf. for example EP-A 297 445 and German Patent 21 36 396).

Removal of the absorbent (and, if necessary, prior desorption of impurities having low solubility in the absorbent by stripping, for example with air) by means of separation processes involving extraction and/or distillation (for example, removal of the absorbent water by distillation, separation of the acid from the aqueous solution by azeotropic distillation or extraction and subsequent removal of the extracting agent by distillation) gives an acid, which is referred to here as crude (meth)acrylic acid.

Owing to a large number of simultaneous and secondary reactions taking place in the course of catalytic gas-phase oxidation, the crude (meth)acrylic acid is not a pure product. Instead, it contains a range of different impurities (as a rule, of the order of $\leq 2\%$ by weight; cf. EP-B 169 254) which mainly consists of aldehydes chemically related to the starting compounds of the catalytic gas-phase oxidation and to the resulting (meth)acrylic acid. As a rule, crude (meth)acrylic acid therefore contains as impurities not only acetic, formic and propionic acid but as a rule also formaldehyde, acetaldehyde, acrolein, methacrolein, propionaldehyde, n-butyraldehyde, benzaldehyde, furfural and crotonaldehyde.

For various applications of (meth)acrylic acid, the impurities contained in the crude (meth)acrylic acid are disadvantageous (cf. for example German Published Application DAS 22 07 184). For example, the induction time of polymerization reactions, ie. the period between reaching the polymerization temperature and the actual start of the polymerization, may not be reproducible or the degree of polymerization may be reduced. Furthermore, the polymers may tend to be discolored.

For such intended uses, it is therefore desirable substantially to separate the impurities from the crude (meth)acrylic acid and to convert crude (meth)acrylic acid into pure (meth)acrylic acid. This is done, as a rule, by distillation, for example by two successive rectification stages for removing impurities which boil at a lower temperature than the (meth)acrylic acid and those which boil at a higher temperature (cf. for example EP-B 102 642).

However, problems are encountered by virtue of the fact that some or all of the aldehydic impurities have physical properties resembling those of (meth)acrylic acid, so that removal of the latter by rectification alone is possible only with the use of an uneconomical number of trays and/or an uneconomical reflux ratio.

DE-B 22 07 184 and British Patent 1 346 737 therefore disclose a process for purifying crude acrylic acid, which comprises adding at least one primary amine, such as hydrazine, phenylhydrazine, aniline, monoethanolamine, ethylenediamine or glycine, to the crude acrylic acid and separating the acrylic acid from the mixture by distillation.

The primary amines evidently bind to a considerable extent the aldehydes contained as impurities, so that one subsequent simple distillative separation stage is sufficient to achieve a high separation effect with regard to the aldehydic impurities.

EP-A 270 999 correspondingly recommends the addition of amino-guanidine and/or a salt thereof in an amount of from 1 to 3 mol per mole of aldehyde present to crude (meth)acrylic acid before the working up by distillation.

DE-A 4 201 697 discloses the addition of an arylsulfonic acid to crude (meth)acrylic acid before the working up by distillation. Similarly, DE-B 2 207 184 also recommends the addition of sulfuric acid prior to working up by distillation. JP-A 117 716/75 recommends the combination phenothiazine/sulfonic acid as a polymerization inhibitor for acrylic acid.

However, the disadvantage of these prior art procedures is that, during the distillation, the distillation apparatuses (in particular the evaporation surface) relatively rapidly become covered with a deposit due to the presence of the above-mentioned additives, since said deposit does not occur when the crude (meth)acrylic acid is worked up by distillation in the absence of these additives (however, such working up by distillation without additives results in only a poor separation effect with regard to the aldehydic impurities contained in the crude (meth)acrylic acid).

The deposits are evidently formed by direct reaction products of the additives with the aldehydic impurities and/or by secondary products formed from said impurities during the working up by distillation.

It is an object of the present invention to provide a process for separating aldehydes from crude (meth)acrylic acid which has been produced by the catalytic gas-phase oxidation method, in which a primary amine and/or a salt thereof is or are added to the crude (meth)acrylic acid and the (meth)acrylic acid is separated from the mixture by distillation, and in which the formation of deposits described is reduced.

We have found that this object is achieved by a process for separating aldehydes from crude (meth)acrylic acid which has been produced by the catalytic gas-phase oxidation method, in which a primary amine and/or a salt thereof is or are added to the crude (meth)acrylic acid and the (meth) acrylic acid is separated from the mixture by distillation, wherein, in addition to the added primary amine and/or its salts, at least one organic sulfonic acid and/or a salt thereof (in particular an ialkali metal salt) is or are added to the crude (meth)acrylic acid before the treatment by distillation. It is advantageous if the organic sulfonic acid is such that, when added to water at 25° C., it reduces the surface tension thereof. As a rule, at least 0.1, but usually not more than 5, mol of at least one organic sulfonic acid is added per mole of added primary amine compound, since no improved effect is achieved above this added amount. Preferably, from 0.5 to 2 mol of at least one organic sulfonic acid are introduced per mole of added primary amine compound.

The addition of the one or more organic sulfonic acids is preferably effected shortly before the working up by distillation, ie. advantageously only the primary amine compound is initially added to the crude (meth)acrylic acid, the mixture is advantageously left to stand for some time (the reaction time depends on the temperature; at from 20 to 100° C., it is from a few minutes to a few hours; the mixture is advantageously left to stand at room temperature), the one or more arylsulfonic acid compounds are then added and working up is subsequently carried out by distillation. Alternatively, the organic sulfonic acid may also be added before or simultaneously with the addition of the primary amine compound. Moreover, the organic sulfonic acid may be added only at the trays of the distillation column, at the top of the column or via the reflux to the column. The addition of the organic sulfonic acid is also successful when deposits have already formed.

Suitable organic sulfonic acids are, for example, alkanesulfonic acids of the general formula $$R^1\text{—}SO_3H,$$

where $R^1$ is $C_1$–$C_{20}$-alkyl. The salts of these alkanesulfonic acids, in particular the alkali metal salts, are also suitable. Methanesulfonic acid and salts thereof are preferred.

Arylsulfonic acids and salts thereof are also useful. Suitable arylsulfonic acid compounds are toluenesulfonic acids, such as p-toluenesulfonic acid, benzenesulfonic acid, phenolsulfonic acids, xylenesulfonic acids, dibutylnaphthalenesulfonic acids and salts thereof, in particular alkali metal salts thereof. However, alkylarylsulfonic acids and salts thereof are very particularly suitable, among which in turn those having only one alkyl substituent are preferred. Aryl is preferably a benzene or naphthalene ring system.

The alkyl radical is advantageously of 5 to 16 carbon atoms.

The alkylbenzenesulfonic acids and salts thereof, ie. compounds of the general formula

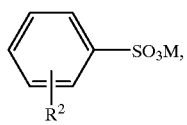

where M is hydrogen or another cation, for example an alkali metal ion, and $R^2$ is $C_5$–$C_{16}$-alkyl, are especially suitable.

$R^2$ is preferably $C_8$–$C_{12}$-alkyl.

Among the alkylbenzenesulfonic acid compounds of the abovementioned general formula, the dodecylbenzenesulfonic acids and salts thereof occupy an outstanding position. This applies in particular to dodecylbenzenesulfonic acid compounds of the general formula

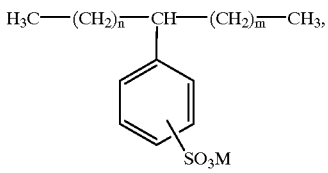

where n and m are integers whose sum must be 9. Very generally, the arylsulfonic acid compound is preferably added in its fully acidic form, ie. the arylsulfonic acid is the preferred additive. This also applies to the alkylsulfonic acid compounds and to aralkylsulfonic acid compounds, which are also suitable as organic sulfonic acid compounds to be added according to the invention.

Suitable primary amines and/or salts thereof to be added are all those whose addition has already been recommended by the prior art. Examples of these (for the sake of simplicity only the amine form is listed; the salts are obtained in a corresponding manner) are hydrazine and derivatives thereof, such as guanylhydrazine (aminoguanidine) and phenylhydrazine, aromatic amines, which are preferably of up to 12 carbon atoms, eg. aniline, o-, m- and p-toluidine and o-, m- and p-aniline, aminocarboxylic acids, eg. glycine, amino alcohols, eg. ethanolamine (2-aminoethanol), as well as chain-like, branched or cyclic aliphatic amines of 1 to 12 carbon atoms, eg. methylamine. Polyfunctional primary amines are of course also suitable, ie. compounds which have more than one, for example 2, 3 or 4, —$NH_2$ groups are also useful. Examples are 1,2-diaminoethane, putrescine (tetramethylenediamine) and cadaverine (pentamethylenediamine). Compounds which have both an —$NH_2$ group and an —$SO_3H$ group, such as sulfanilic acid (4-aminobenzenesulfonic acid), are of course also suitable.

Suitable salts of the primary amines to be added are in particular their bicarbonate, nitrate, sulfate or chloride. Aminoguanidine bicarbonate may be mentioned by way of example, said compound being the preferably added aminoguanidine compound. The added combination particularly advantageously consists exclusively of aminoguanidine bicarbonate and dodecylbenzenesulfonic acid.

The amount of primary amines of their salts added to the crude (meth)acrylic acid is up to 5 mols per mol of aldehydic inpurities. Preferably, from 1 to 3 mols of amine or amine salt is added per mol of said impurities.

The novel process can of course also be used for separating aldehydes from (meth)acrylic acid which is not crude (meth)acrylic acid, ie. has been obtained by a method other than catalytic gas-phase oxidation of $C_3$- or $C_4$-compounds and therefore contains aldehydic impurities for other reasons.

Working up of the crude (meth)acrylic acid modified according to the invention by distillation is preferably carried out at reduced pressure, advantageously $\leq 100$, as a rule from 10 to 100, mbar. Correspondingly, the associated boiling point is usually from 70 to 105° C.

The novel process is particularly important in the case of crude methacrylic acid whose preparation by catalytic gas-phase oxidation starts from methacrolein, especially when the methacrolein is produced by catalytic gas-phase oxidation of tert-butanol, isobutane or isobutene or by reacting formaldehyde with propionaldehyde according to EP-B 92 097 or EP-B 58 927 and in turn especially when the catalytic gas-phase oxidation of the tertbutanol, isobutane or isobutene is carried out with the use of a catalytically active material of the general formula I

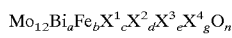  (I), where
X$^1$ is nickel and/or cobalt,
X$^2$ is thallium, an alkali metal and/or an alkaline earth metal,
X$^3$ is phosphorus, arsenic, boron, antimony, tin, cerium, lead, niobium and/or tungsten,
X$^4$ is silicon, aluminum, titanium and/or zirconium,
a is from 0.5 to 5.0
b is from 0.01 to 3.0
c is from 3.0 to 10.0
d is from 0.02 to 2.0
e is from 0 to 5.0
g is from 0 to 10 and
n is a number which is determined by the valency and frequency of the elements other than oxygen in I, at 300 to 400° C. and, apart from the specific temperature range, otherwise according to the conditions of prior German Application P 40 23 239.5 (O.Z. 0050/41774), and the resulting methacrolein is used for further oxidation without intermediate purification. The novel process has proven useful in particular when the catalytic gas-phase oxidation of the methacrolein is carried out, apart from the specific temperature range, according to prior German Application P 41 32 263.0 (O.Z. 0050/42719) at from 200 to 350° C. or according to prior German Application P 41 32 684.9 (O.Z. 0050/42725) at from 250 to 400° C.

The novel process is of course carried out in the presence of polymerization inhibitors, such as air, hydroquinone, hydroquinone monoethyl ether, paranitrosophenol, paramethoxyphenol or phenothiazine.

They are usually used in amounts of from 50 to 1000 ppm, based on the crude (meth)acrylic acid.

The novel process has proven particularly advantageous in the presence of aromatic hydroxy compounds, such as hydroquinone and hydroquinone monomethyl ether, as polymerization inhibitors.

The novel process is distinguished by the fact that it provides a particularly effective separation by distillation of aldehydic impurities from crude (meth)acrylic acid on the one hand and substantially suppresses accompanying formation of deposits on the other hand. The novel process is therefore particularly suitable for a continuous procedure, as described in DE-A 42 01 697.

EXAMPLES

Example 1

Methacrolein was prepared according to Example 1 of EP-B 58 927, by condensation of formaldehyde and propionaldehyde and subsequent azeotropic distillation. An aqueous methacrylic acid solution was obtained from the methacrolein according to the process example of EP-B 297 445 (catalytic gas-phase oxidation). This was stripped at from 50 to 70° C. with the synthesis air (fresh air) used for the oxidation (for amount of fresh air, see Table 1 of EP-A 297 445) and then extracted with isooctanoic acid according to Example 6 of Patent 54,354 of the German Democratic Republic, and the resulting methacrylic acid/isooctanoic acid mixture was separated by distillation according to Example 10 of said publication. 944 ppm by weight (based on the crude acid) of aminoguanidine bicarbonate were added to the crude methacrylic acid thus obtained, and the resulting mixture was left to stand at room temperature for about 6 hours with gentle stirring.

The crude methacrylic acid treated in this manner was then fed continuously (0.5 l/h) to a rectification column for separation, via the top, of impurities having boiling points lower than the boiling point of methacrylic acid. The bottom product discharged from this column was transferred continuously to a still, and the methacrylic acid was distilled off via the top in high purity (still temperature: 105° C., pressure: 100 mbar, aldehyde purity of the resulting methacrylic acid: <1 ppm of CO (calculated as methacrolein)). The rectification column used was an insulated, double-walled packed column silvered on both walls (diameter: 50 mm, length: 1 m, 5 mm wire mesh coils, bottom temperature: 105° C., pressure: 100 mbar).

After continuous operation for only 2 hours, the bottom of the rectification column and the still were found to contain an extensive solid precipitate (russet sludge) which led on the one hand to the formation of deposits, which hindered heat transmission, and on the other hand to blockage of pipes and pumps, so that the plant had to be shut down after 3 hours.

The Example was repeated under the same conditions, except that an equimolar amount, based on the added amount of aminoguanidine bicarbonate, of dodecylbenzenesulfonic acid was additionally introduced prior to working up by distillation.

After continuous operation for 48 hours, there was still no solid deposit in the bottom of the rectification column and in the still. The aldehyde purity of the resulting methacrylic acid was likewise <1 ppm of CO (calculated as methacrolein).

In both cases, the process was carried out in the presence of 200 ppm (based on the weight of the crude acids) of hydroquinone monomethyl ether as polymerization inhibitor.

Example 2

In a continuously operated glass rectification column whose evaporator was a glass convection reboiler which was heated by means of a metallic, electrically heatable element, 140 ml/h of a crude acrylic acid which had been obtained by catalytic gas-phase oxidation of acrolein according to Example B1 of DE-A 43 02 991 and subsequent working up of the reaction gases according to Example B1 of DE-A 21 36 396 were fed continuously via the evaporator. The same amount of crude acid was removed continuously from the evaporator. The evaporated crude acid was condensed above the rectification column and transferred quantitatively as a reflux back to the top of the column. The column was stabilized by means of phenothiazine via the top of the column. 1100 ppm, based on the weight of the crude acrylic acid, of aminoguanidine bicarbonate had been added to said acrylic acid before the latter had been fed into the evaporator. During the rectification, a deposit was formed on the heating element, the weight of which deposit was determined after an operating time of 40 hours. The result is shown in the Table below. It also shows the results which were obtained when 1.5 mol, per mole of aminoguanidine compound present, of various organic sulfonic acids were added to the crude acrylic acid immediately before it was fed into the evaporator.

TABLE

| Added sulfonic acid | Amount of deposit (mg) |
|---|---|
| — | 400 |
| p-Toluenesulfonic acid | 50 |
| Dodecylbenzenesulfonic acid | 20 |
| Methanesulfonic acid | 10 |
| Xylenesulfonic acid | 50 |
| Dibutylnaphthalenesulfonic acid | 70 |

Example 3

The procedure was as in Example 2, except that 450 ppm of hydrazine monohydrate were added instead of 1100 ppm of aminoguanidine bicarbonate. After an operating time of 5 hours, the deposit formed amounted to 2200 mg. When 1.5 mol of dodecylbenzenesulfonic acid per mole of added hydrazine were also introduced into the crude acrylic acid immediately before it was fed into the evaporator, the amount of deposit formed was still less than 10 mg even after operation for 40 hours.

We claim:

1. A process for purifying a (meth)acrylic acid contaminated with aldehydes which consists essentially of adding jointly to the (meth)acrylic acid contaminated with aldehydes both a hydrazine and/or a derivative thereof, and at least one organic sulfonic acid and/or one of its salts, and thereafter separating the (meth)acrylic from the resulting mixture by distillation, whereby the resulting (meth)acrylic is substantially free of the aldehydes and the formation of undesirable deposits during the distillation is substantially suppressed.

2. The process of claim 1 wherein the hydrazine derivative is aminoguanidine and/or a salt thereof.

3. The process of claim 1 wherein hydrazine derivative is aminoguanidine bicarbonate.

4. A process as defined in claim 1, wherein the added sulfonic acid compound is dodecylbenzenesulfonic acid.

5. A process as defined in claim 1, wherein the (meth) acrylic acid contaminated with aldehydes is a crude (meth) acrylic acid produced by the catalytic gas-phase oxidation method.

6. A process as defined in claim 1, which is carried out continuously.

* * * * *